United States Patent [19]
Ranson et al.

[11] Patent Number: 5,572,030
[45] Date of Patent: Nov. 5, 1996

[54] METHOD FOR DETERMINING PARAMETER OF HYDROCARBON

[75] Inventors: Aaron Ranson, S. Antonio, Venezuela; Fernando Arroyo, Babson Park, Mass.; Adriano Parisi, Los Nuevos Teques.; Hernan Prieto, Los Teques, both of Venezuela

[73] Assignee: Intevep, S.A., Caracas, Venezuela

[21] Appl. No.: 585,000

[22] Filed: Jan. 11, 1996

Related U.S. Application Data

[63] Continuation of Ser. No. 231,424, Apr. 22, 1994, abandoned.

[51] Int. Cl.$^6$ .................................................. G01N 21/35
[52] U.S. Cl. ....................................... 250/339.12; 395/202
[58] Field of Search .................... 250/339.12, 339.09, 250/339.11, 339.07, 341.5; 395/932, 911, 22

[56] References Cited

U.S. PATENT DOCUMENTS

| | | | |
|---|---|---|---|
| 5,015,856 | 5/1991 | Gold | 250/339.06 |
| 5,218,529 | 6/1993 | Meyer et al. | 250/413.01 |
| 5,265,031 | 11/1993 | Malczewaki | 395/911 |

Primary Examiner—Davis L. Willis
Assistant Examiner—Richard Hanig
Attorney, Agent, or Firm—Bachman & LaPointe, P.C.

[57] ABSTRACT

A method for evaluating a hydrocarbon so as to determine a desired parameter of the hydrocarbon includes the steps of providing a hydrocarbon to be evaluated, obtaining a near-infrared signal from the hydrocarbon, codifying the near-infrared signal so as to reduce the signal to a number of points, providing a neural network trained for correlating the number of points to the desired parameter and processing the number of points with the neural network so as to determine the desired parameter.

16 Claims, 9 Drawing Sheets

METHOD FOR DETERMINING PARAMETER OF HYDROCARBON

This is a continuation of application Ser. No. 08/231,424 filed on Apr. 22, 1994.

BACKGROUND OF THE INVENTION

The invention relates to a method for evaluating a substance, especially a hydrocarbon fuel such as gasoline, diesel fuel, naphtha, jet fuel, kerosene and the like, to determine one or more parameters of the substance.

Accurate methods for measuring parameters of fuels such as gasoline are desirable. It is especially useful to obtain accurate measurements of parameters such as octane numbers, Reid vapor pressure and the like so that products can be supplied to customers which accurately meet the customers specifications.

Near infrared (NIR) spectroscopy has been found to be useful in evaluating certain substances because certain bands of the NIR signal are indicative of parameters of the substance. For example, U.S. Pat. No. 4,963,745 to Maggard discloses a process for measuring octane of gasoline using NIR spectroscopy and mathematical processing using derivatives. This method, sometimes referred to as multi-variate analysis, is useful in measuring some parameters. However, the method requires a high signal-to-noise ratio and long-term stability, and further requires a linear correlation between the NIR spectrum data obtained and the parameter to be determined.

In accordance with the foregoing, it is the principal object of the present invention to provide a method for evaluating desired parameters of a substance, particularly a hydrocarbon such as gasoline or other types of fuel using NIR spectroscopy wherein accurate readings are obtained despite non-linearity of the relation between the input NIR signal and the output parameter to be determined.

It is a further object of the invention to provide a method for evaluation which provides accurate determinations despite potentially large amounts of "noise" or corrupted data in the NIR signal.

It is still another object of the invention to provide a method for evaluation wherein measurements are obtained "on-line."

Other objects and advantages will appear herein below.

SUMMARY OF THE INVENTION

The foregoing objects and advantages are readily attained by the present invention.

In accordance with the invention, desired parameters of a hydrocarbon, preferably a hydrocarbon fuel such as gasoline, diesel fuel, naphtha, jet fuel, kerosene and the like are determined by a method comprising the steps of providing a hydrocarbon to be evaluated, obtaining a near-infrared signal from the hydrocarbon, codifying the near-infrared signal so as to reduce the signal to a number of points, providing a neural network trained for correlating the number of points to the desired parameter and processing the number of points with the neural network so as to determine the desired parameter.

Parameters which may accurately be defined need not be linearly related to the NIR signal and may include Reid vapor pressure, simulated distillation values, research octane number, motor octane number, oxygen content, specific gravity, cetane number, bromine number, aniline point, smoke point, and combinations thereof, as well as numerous other parameters.

Further, while the preferred application of the method is to hydrocarbons, numerous other substances such as food, chemicals, and the like may also be evaluated in accordance with the method of the present invention.

BRIEF DESCRIPTION OF THE DRAWINGS

A detailed description of the preferred embodiments of the invention follows, with reference to the attached drawings, wherein.

DETAILED DESCRIPTION

The invention relates to a method for evaluating a substance, particularly a hydrocarbon such as gasoline, diesel fuel, kerosene and the like, so as to determine, preferably in an on-line manner, one or more desired parameters of the hydrocarbon.

As set forth above, near-infrared (NIR) spectroscopy is known to provide a signal which corresponds to various parameters of the material in question. However, the relation is frequently non-linear in the field of hydrocarbon fuels, and conventional methods for evaluating the signal, such as those described in U.S. Pat. No. 4,963,745, require a linear relationship.

In accordance with the invention, a method is provided whereby a neural network is trained and used so as to provide determinations of desired parameters of a hydrocarbon from an NIR signal whether the relation is linear or non-linear. Further, the method according to the invention provides accurate determinations even when subjected to relatively large amounts of "noise" or corrupted data in the NIR signal. Still further, the method according to the invention may be utilized to determine if a given property is present, if it is within a given range, and if it can be grouped along with other spectra in a family, as well as to predict the magnitude of a parameter or property based on the correlation between the NIR spectra and a related expected value.

Figure 1:
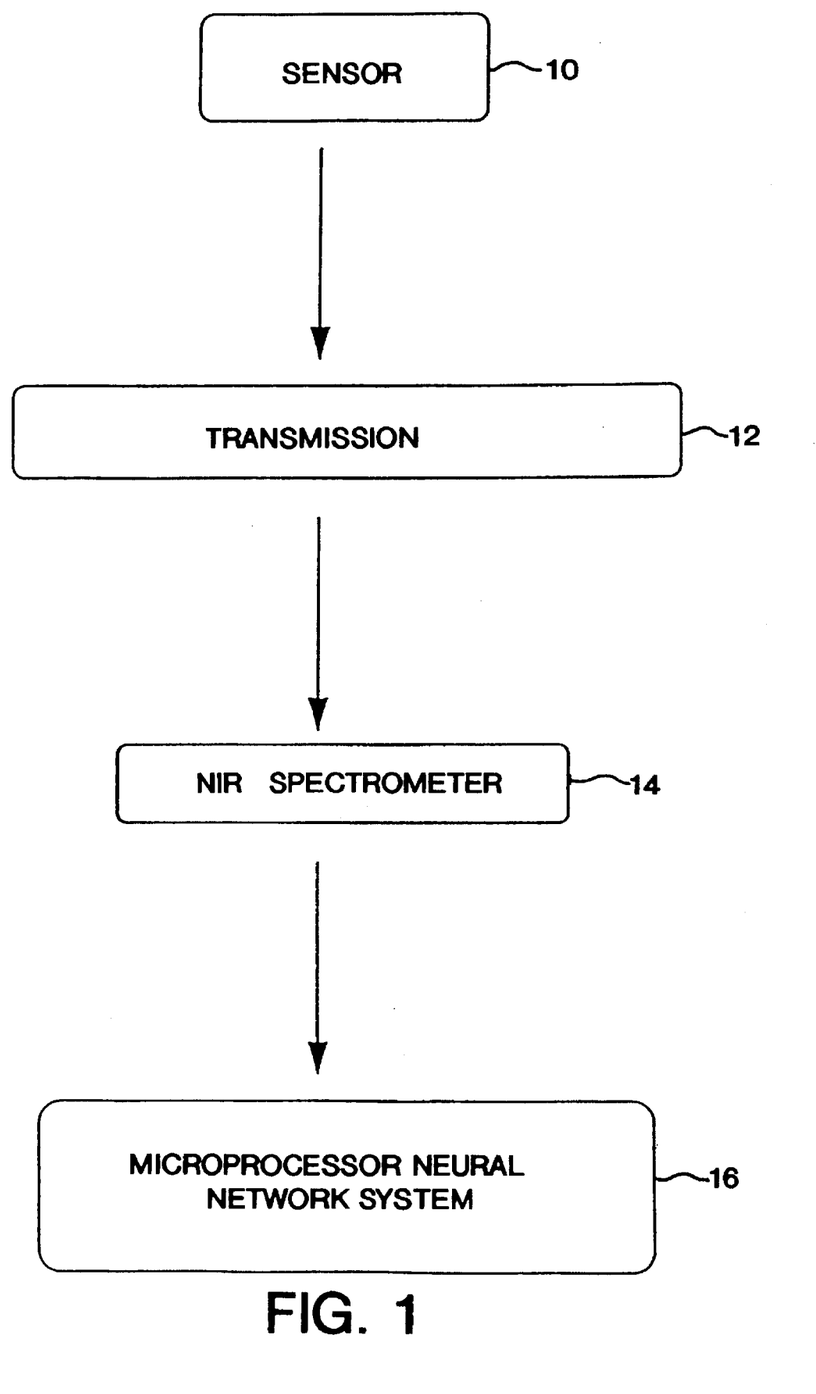
FIG. 1 is a schematic diagram of an apparatus for carrying out the method of the invention.
Figure 2:
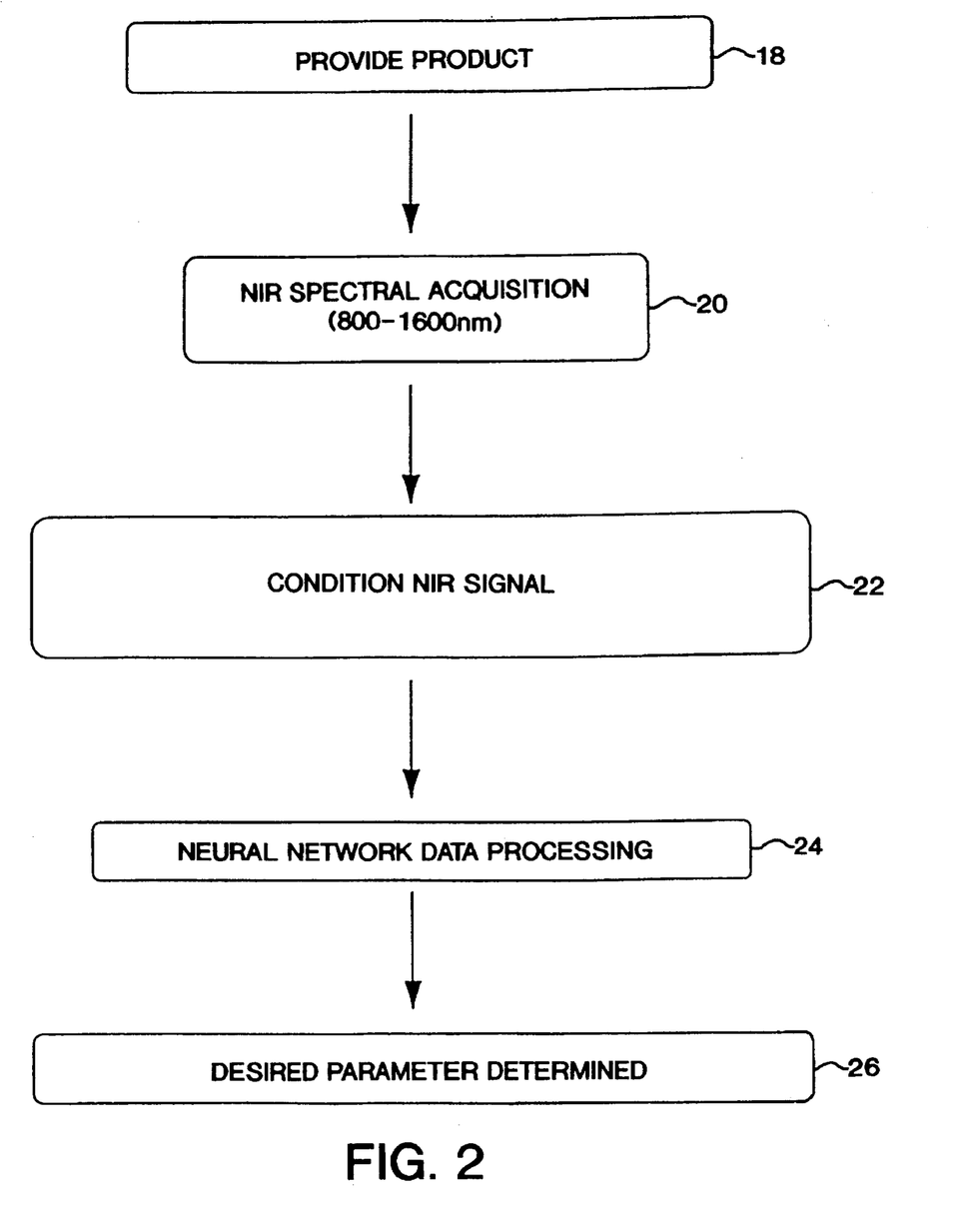
FIG. 2 is a flow chart illustrating the steps of the method of the invention.

FIG. 1 schematically illustrates an apparatus for carrying out the method of the invention, and FIG. 2 is a flow chart illustrating the steps of the method according to the invention.

Referring to FIG. 1, a sensor 10 is provided for obtaining NIR signals of the hydrocarbon or other substance to be evaluated. Sensor 10 may be a sensor for obtaining reflective or transmittance NIR spectra from the hydrocarbon. Such sensors are well known in the art and may be used in accordance with the invention to obtain the desired NIR spectra in an on-line manner. A typical transmittance sensor may include, for example, a conduit (not shown) through which the hydrocarbon or other substance flows and two collimators on the conduit which direct a light beam through the hydrocarbon. Of course, numerous other types of sensors or other instruments for obtaining the desired NIR spectra are well known in the art and suitable for use in accordance with the present invention.

The system according to the invention further includes a transmission member 12 for conveying the NIR spectrum so obtained from sensor 10 to a spectrometer 14 for processing the signal from sensor 10 so as to provide base line correction of the signal and to reduce the signal to a desired number of points. Transmission member 12 may be a suitable optic fiber or the like.

The system also includes a trained neural network 16 for receiving the conditioned signal from spectrometer 14. Network 16 is "trained" to determine one or more desired parameters of the hydrocarbon based upon the absorbance values of the points of the conditioned signal. Network 16 processes the signal received from spectrometer 14 so as to provide the desired parameter.

As shown in FIG. 2, step 18 calls for the provision of hydrocarbon to be measured and evaluated, preferably in an on-line manner. In accordance with the invention, the NIR spectrum of the hydrocarbon is measured in step 20 at a wavelength of between about 800 nm to about 1600 nm. In this range, it is further preferable to select a wavelength of between about 800 nm to about 1050 nm (which corresponds to the third overtone and its recombination bands), or between about 1100 nm to about 1500 nm (which corresponds to the second overtone and its recombination bands). The foregoing ranges are particularly desirable because bands corresponding to methyl, methylene, oleophilic and aromatic content are concentrated therein.

Numerous spectrometers are suitable and commercially available for obtaining the desired NIR spectra or signal. Examples of suitable spectrometers include model SC 300 supplied by Guidewave, Pioneer 1024 from Perkin Elmer, and others.

The NIR signal obtained as above is then conditioned in step 22 in accordance with the invention so as to codify the signal by correcting the spectrum base line and reducing the signal to a suitable number of points which are to be processed by the neural network to obtain the desired hydrocarbon parameters.

Signal conditioning may be carried out using any suitable PC such as, for example, a Sun Corporation work station computer in a UNIX operating system, or in any other conventional manner so as to correct and reduce the NIR signal to the points to be supplied to the neural network.

In step 24, the points from step 22 are processed by the neural network so as to provide a determination of the desired parameter (step 26).

A neural network is a layered network including an input layer having a network input and an output layer having a network output. One or more hidden layers are positioned between the input layer and the output layer for processing input information according to a weighted sum of network inputs.

Points from step 22 are entered or input to the network input of the input layer and processed by the layers of the network so as to provide the desired parameter as output from the network output of the output layer. The input data is processed by a sigmoid transfer function between each layer of the network. The transfer functions convey a signal to the next layer of the network. The combination of input received by a layer serves to define the output of that layer, with various portions of the input being assigned more or less weight based upon the aforementioned weighted values.

The weighted values are determined through a process known in the art as training, whereby a number of known input and output values are provided to the network, and additional values are then processed by the network, with the weighted values being altered after each run until the error is consistently below an acceptable value of error.

Neural networks are well known to those skilled in the art. Suitable neural networks may be generated with commercially available software including but not limited to Planet 5.6, Unscrambler, and Neuralwave.

The training of neural networks is also well known in the art, and numerous techniques such as back propagation, supervised learning and the like are known to the person skilled in the art. An example of a training procedure is set forth below with reference to FIG. 3.

The input layer of the neural network has a number of nodes for receiving the points of the codified NIR signal. The number of nodes to be utilized is selected so as to be great enough to provide reliable determinations, but small enough that the neural network is not overly complicated. It has been found, in accordance with the invention, that Reid vapor pressure of a gasoline may be determined using a range of between about 30 to about 100 input nodes.

The nodes of the input layer process the incoming points in accordance with the training of the neural network to provide partially processed signals to the intermediate hidden layer(s) which further process the signals so as to provide an output from the output layer corresponding to the desired parameter.

Propagation from the input layer to the intermediate layer is achieved by sigmoid function which serves to determine the output of a node (j) based upon input received by the node from nodes (i) of a preceding layer. The sigmoid function is as follows:

$$O_j = f\left( \sum_{i=0}^{n} W_{ji} \cdot I_i \right),$$

wherein $I_i$ is the output value of node i;

$W_{ji}$ is the weighted value between nodes j and i; and $O_j$ is the output value of node j.

The sigmoid transfer function used in conjunction with the foregoing is preferably as follows:

$$f(x) = 1/(1+e^{-x})$$

wherein $$x = \left( \sum_{i=0}^{n} W_{ji} \cdot I_i \right).$$

The intermediate layer typically has a number of nodes which is less than that of the input layer and more than that of the output layer. For example, if the input layer has 30–100 nodes, the intermediate layer may preferably have between about 3 to about 15 nodes. The nodes of the intermediate layer serve to process incoming signals from the input layer according to an additional set of weighted values which are also determined during the training of the neural network. Propagation from the intermediate layer to the output layer is also preferably accomplished as set forth above so as to provide the desired output.

Sigmoid transfer functions are particularly suitable in processing data from layer to layer in the network because they are useful in modelling non-linear patterns or functions.

In accordance with the invention, the hydrocarbon to be evaluated may suitably be gasoline, diesel fuel, kerosene, naphtha, jet fuel and the like. While numerous parameters of the hydrocarbon may be evaluated, specific examples include Reid vapor pressure, simulated distillation values, research octane number, motor octane number, oxygen content, specific gravity, cetane number for diesel fuel, bromine number for diesel fuel or gasoline, aniline point, smoke point and the like. Many of the foregoing are non-linearly related to the NIR signal and could not therefore be determined according to conventional methods.

Figure 3:
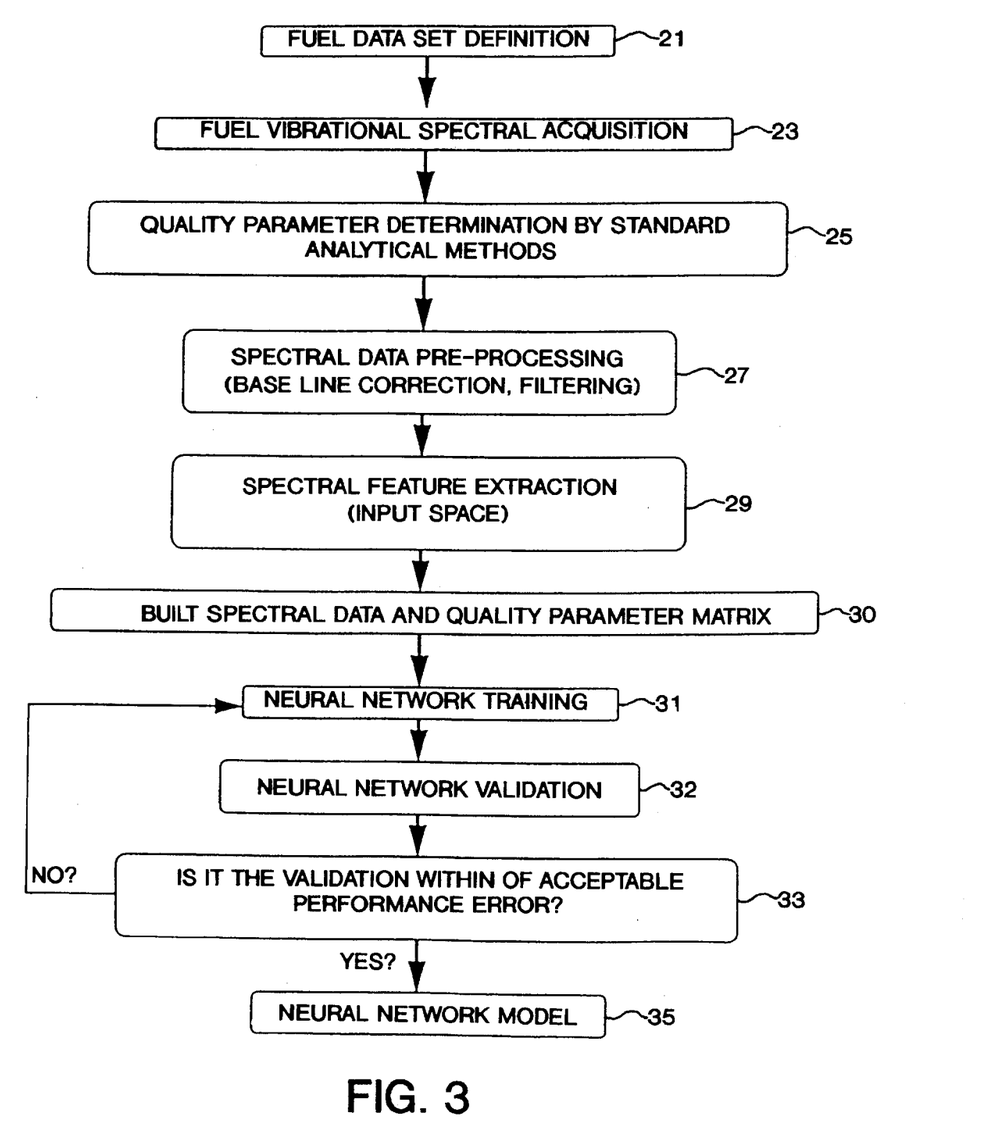
FIG. 3 is a flow chart illustrating the training of a neural network for use in the method of the present invention.

FIG. 3 illustrates a training process for training a neural network for use in accordance with the invention.

Initially, a computer configured as a neural network is provided. A set of data must then be provided with which to initiate training of the network. Step 21 in FIG. 3 shows the selection of the family. In step 23, NIR spectra are obtained for each member of the family.

The desired parameter for each member of the family is then determined in step 25 using standard analytical methods.

The spectra obtained in step 23 are then conditioned in steps 27 and 29. Step 27 provides the base line correction of the signal which, in step 29, is reduced so as to extract the desired number of points to be inputted to the network.

Two matrices are then built, one with the points obtained in step 29, and the other with the parameter values determined analytically in step 25. Through the training process, and using the two matrices, final weighted values for the input to intermediate layer and for the intermediate to output layer are calculated. The randomized initial weighted values are adjusted and optimized by an iteration process carried out in steps 31 and 32. With additional samples or with members of the family of data, readings provided by the network are compared in step 33 with those expected in accordance with step 25. At each comparison, back propagation techniques or supervised learning or any other known training technique may be used to adjust the weighted values between nodes until the network provides determinations which are consistently within an acceptable degree of error. Once this occurs, the network is fully trained and ready for use. In step 35, the network is placed on line to determine quantitative parameters without requiring conventional methods which may not be carried out on line or even at the production site.

EXAMPLE 1

This example illustrates the training of a neural network and use of the trained neural network in accordance with the method of the invention to determine Reid vapor pressure of gasoline.

In this example, a family of 56 typical gasolines was selected as the set of data. This family included gasoline rated as regular, super and premium.

NIR spectra were obtained for each member of the family, in this example using a vis-NIR fiber optics based Guidewave Model 300A spectrometer using a 1 cm fuse silica cuvette at a wavelength range of 800 nm to 1600 nm using a one (1) nm resolution.

Standard analytical techniques were then used to measure the actual Reid vapor pressure of each member of the family. The measurement was carried out according to ASTM D-323-82. The range of the selected Reid vapor pressure was 45.5 kPa to 82.7 kPa (6.6 psi to 12 psi). This range corresponds to typical Reid vapor pressures for commercial gasoline. The measured values are set out below in Table I.

TABLE I

| Super Gasoline | Measured RVP (psi) | Regular Gasoline | Measured RVP (psi) | Premium Gasoline | Measured RVP (psi) |
|---|---|---|---|---|---|
| ap.001 | 7.65 | mp.001 | 7.94 | sp.001 | 7.21 |
| ap.002 | 7.68 | mp.002 | 7.96 | sp.002 | 6.66 |
| ap.003 | 8.24 | mp.003 | 8.15 | sp.003 | 6.66 |
| ap.004 | 8.35 | mp.004 | 8.61 | sp.004 | 7.42 |
| ap.005 | 8.43 | mp.005 | 8.61 | sp.005 | 7.63 |
| ap.006 | 8.51 | mp.006 | 8.84 | sp.006 | 7.42 |
| ap.007 | 8.84 | mp.007 | 9.02 | sp.007 | 7.90 |
| ap.008 | 9.03 | mp.008 | 9.28 | sp.008 | 7.06 |
| ap.009 | 9.40 | mp.009 | 9.71 | sp.009 | 8.20 |
| ap.010 | 9.56 | mp.010 | 10.05 | sp.010 | 8.48 |
| ap.011 | 9.87 | mp.011 | 10.23 | sp.011 | 8.64 |
| ap.012 | 9.73 | mp.012 | 10.49 | sp.012 | 8.71 |
| ap.013 | 9.98 | mp.013 | 10.06 | sp.013 | 8.80 |
| ap.014 | 10.00 | mp.014 | 10.95 | sp.014 | 9.10 |
| ap.015 | 10.40 | mp.015 | 11.08 | sp.015 | 9.29 |
| | | | | sp.016 | 9.42 |
| | | | | sp.017 | 9.68 |
| | | | | sp.018 | 10.02 |
| | | | | sp.019 | 10.34 |
| | | | | sp.020 | 10.76 |
| | | | | sp.021 | 10.84 |
| | | | | sp.022 | 11.09 |
| | | | | sp.023 | 11.16 |
| | | | | sp.024 | 11.52 |
| | | | | sp.025 | 11.64 |
| | | | | sp.026 | 11.99 |

Figure 4:
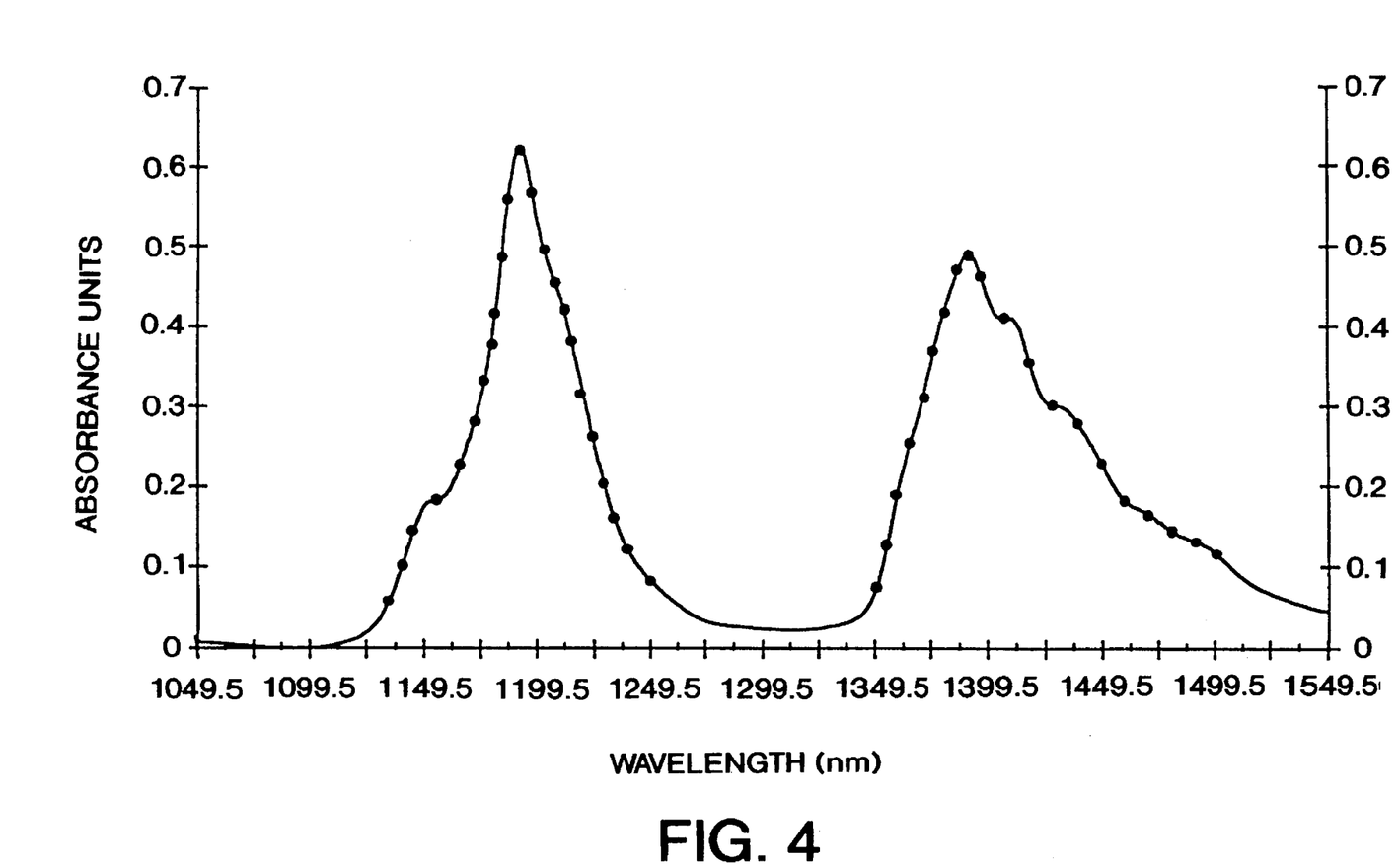
FIG. 4 illustrates the second overtone and its recombination bands for a typical processed spectrum as illustrated in Example 1.

The second overtone of the NIR spectra and its recombination bands, at a wavelength range between about 1100 nm to about 1500 nm, was measured for each member of the family and conditioned in accordance with the invention so as to provide 47 points. The network was configured to have 47 input nodes in the input layer for these points. FIG. 4 illustrates a curve corresponding to the points selected.

The points and analytically measured parameters were then arranged into matrices which were inputted to the network to begin the training process. Fifty of the fifty-six members of the family were arranged in the matrices. The remaining six samples were held for use in validating the neural network after training. In this example, a predicted value is acceptable if it is within 0.5 psi of the ASTM measured value.

Tables II–IV set forth below contain the no noise predictions of RVP values and ASTM measurements of the fifty samples used to train the network. Table V contains predicted and ASTM values for the validation set. As shown, the average error and standard deviation were acceptable. The trained neural network was then ready and placed on line for measuring Reid vapor pressure in accordance with the invention.

TABLE II

| Gasoline Super | RVP ASTM D 323 | RVP Predicted | Error |
| --- | --- | --- | --- |
| ap.002 | 7.68 | 7.76 | 0.08 |
| ap.003 | 8.24 | 8.27 | 0.03 |
| ap.004 | 8.35 | 8.33 | 0.02 |
| ap 005 | 8.43 | 8.43 | 0.00 |
| ap.006 | 8.51 | 8.69 | 0.18 |
| ap.007 | 8.84 | 8.89 | 0.05 |
| ap.008 | 9.03 | 9.26 | 0.23 |
| ap.009 | 9.40 | 9.26 | 0.14 |
| ap.010 | 9.56 | 9.48 | 0.08 |
| ap.011 | 9.87 | 9.81 | 0.06 |
| ap.012 | 9.73 | 9.61 | 0.12 |
| ap.13 | 9.98 | 10.03 | 0.05 |
| ap.014 | 10.00 | 10.13 | 0.13 |
| Average Error | 0.09 | | |
| Std Dev. Error | 0.07 | | |

TABLE III

| Gasoline Regular | RVP ASTM D 323 | RVP Predicted | Error |
| --- | --- | --- | --- |
| mp.002 | 7.96 | 8.04 | 0.08 |
| mp.003 | 8.15 | 8.33 | 0.17 |
| mp.004 | 8.61 | 8.44 | 0.17 |
| mp.005 | 8.73 | 8.73 | 0.00 |
| mp.006 | 8.84 | 9.06 | 0.22 |
| mp.007 | 9.02 | 8.81 | 0.21 |
| mp.008 | 9.28 | 9.43 | 0.15 |
| mp.009 | 9.71 | 9.66 | 0.05 |
| mp.010 | 10.05 | 9.97 | 0.08 |
| mp.011 | 10.23 | 10.26 | 0.03 |
| mp.012 | 10.49 | 10.63 | 0.14 |
| mp.013 | 10.06 | 10.33 | 0.27 |
| mp.014 | 10.95 | 10.77 | 0.18 |
| Average Error | 0.13 | | |
| Std Dev. Error | 0.08 | | |

TABLE IV

| Gasoline Premium | RVP ASTM D 323 | RVP Predicted | Error |
| --- | --- | --- | --- |
| sp.002 | 6.66 | 7.05 | 0.45 |
| sp.003 | 7.21 | 7.23 | 0.02 |
| sp.004 | 7.42 | 7.36 | 0.06 |
| sp.005 | 7.63 | 7.47 | 0.16 |
| sp.006 | 7.42 | 7.51 | 0.09 |
| sp.007 | 7.90 | 7.91 | 0.01 |
| sp.008 | 7.96 | 7.89 | 0.07 |
| sp.009 | 8.20 | 8.11 | 0.09 |
| sp.010 | 8.48 | 8.53 | 0.05 |
| sp.011 | 8.64 | 8.64 | 0.00 |
| sp.012 | 8.71 | 8.58 | 0.13 |
| ap.013 | 8.80 | 8.76 | 0.04 |
| sp.014 | 9.10 | 9.10 | 0.00 |
| sp.016 | 9.42 | 9.47 | 0.05 |
| sp.017 | 9.68 | 9.70 | 0.02 |
| sp.018 | 10.02 | 10.06 | 0.04 |
| sp.019 | 10.34 | 10.53 | 0.19 |
| sp.020 | 10.76 | 10.96 | 0.20 |
| sp.021 | 10.84 | 10.89 | 0.05 |
| sp.022 | 11.09 | 11.06 | 0.03 |
| sp.023 | 11.16 | 11.15 | 0.01 |
| sp.024 | 11.52 | 11.52 | 0.01 |
| sp.025 | 11.64 | 11.59 | 0.05 |
| sp.026 | 11.99 | 11.91 | 0.08 |
| Average Error | 0.8 | | |
| Std Dev. Error | 0.10 | | |

TABLE V

| Gasoline validation test | RVP ASTM D 323 | RVP Predicted | Error |
| --- | --- | --- | --- |
| ap.001 | 7.65 | 7.47 | 0.19 |
| ap.015 | 10.40 | 10.19 | 0.21 |
| mp.001 | 7.94 | 7.58 | 0.36 |
| mp.015 | 11.08 | 11.38 | 0.30 |
| sp.001 | 7.21 | 6.95 | 0.26 |
| sp.015 | 9.29 | 9.05 | 0.24 |
| Average Error | 0.09 | | |
| Std Dev. Error | 0.07 | | |

Figure 5:
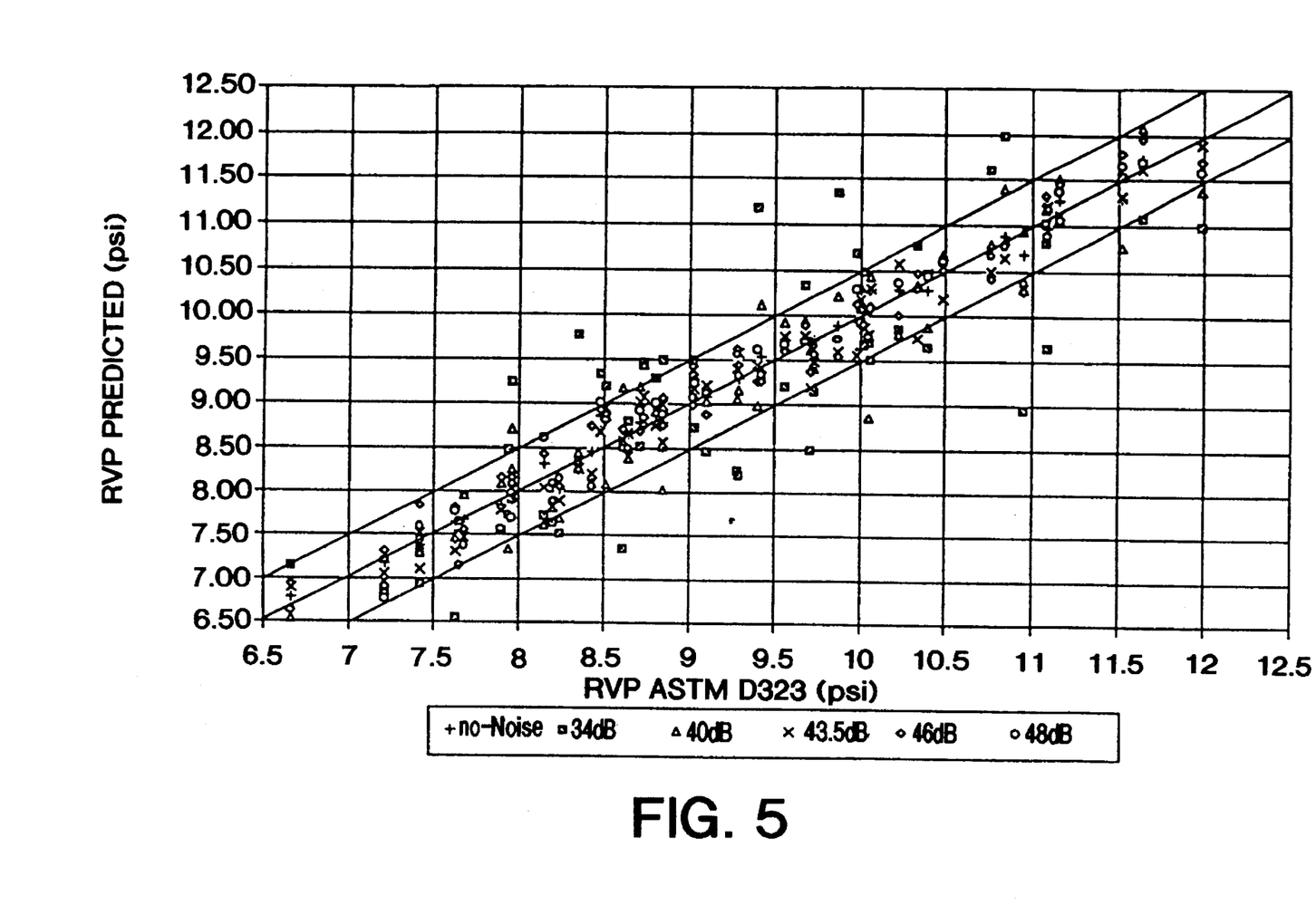
FIG. 5 illustrates RVP values predicted according to the invention compared to actual RVP values measured according to ASTM D-323.
Figure 6:
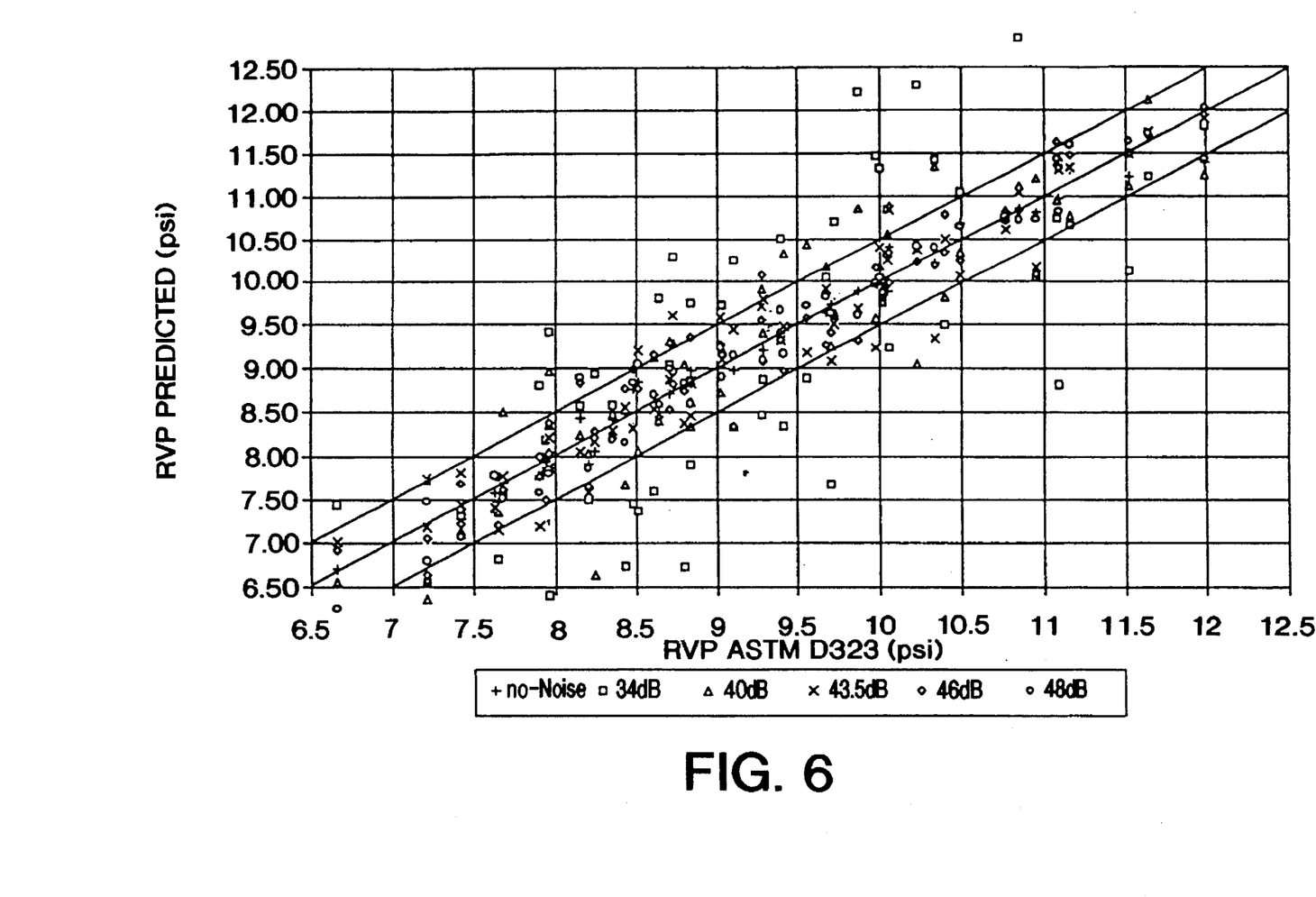
FIG. 6 illustrates conventionally predicted RVP values compared to actual RVP values measured according to ASTM D-323.

RVP values were then predicted according to the invention using the second overtone and recombination band of the fifty-six spectra. The RVP values so predicted are plotted in FIG. 5 versus actual values measured according to ASTM D-323. For each gasoline, five additional predictions were made while subjecting the signal to Gaussian noise values of 34 dB, 40 dB, 43.5 dB, 46 dB and 48 dB. These values are also plotted on FIG. 5. As shown, the neural network method provides predictions of RVP values which are within acceptable error tolerances even when the signal is subjected to relatively large amounts of noise.

To further illustrate the advantages of the present invention, RVP values for the same gasolines were predicted according to conventional multivariate (Partial Least Square) analysis. The values are set forth verses actual measurements taken by ASTM D-323, with no noise and with added Gaussian noise as set forth above. As illustrated, a far greater number of predictions made according to conventional methods fall outside of acceptable levels of error.

EXAMPLE 2

Figure 7:
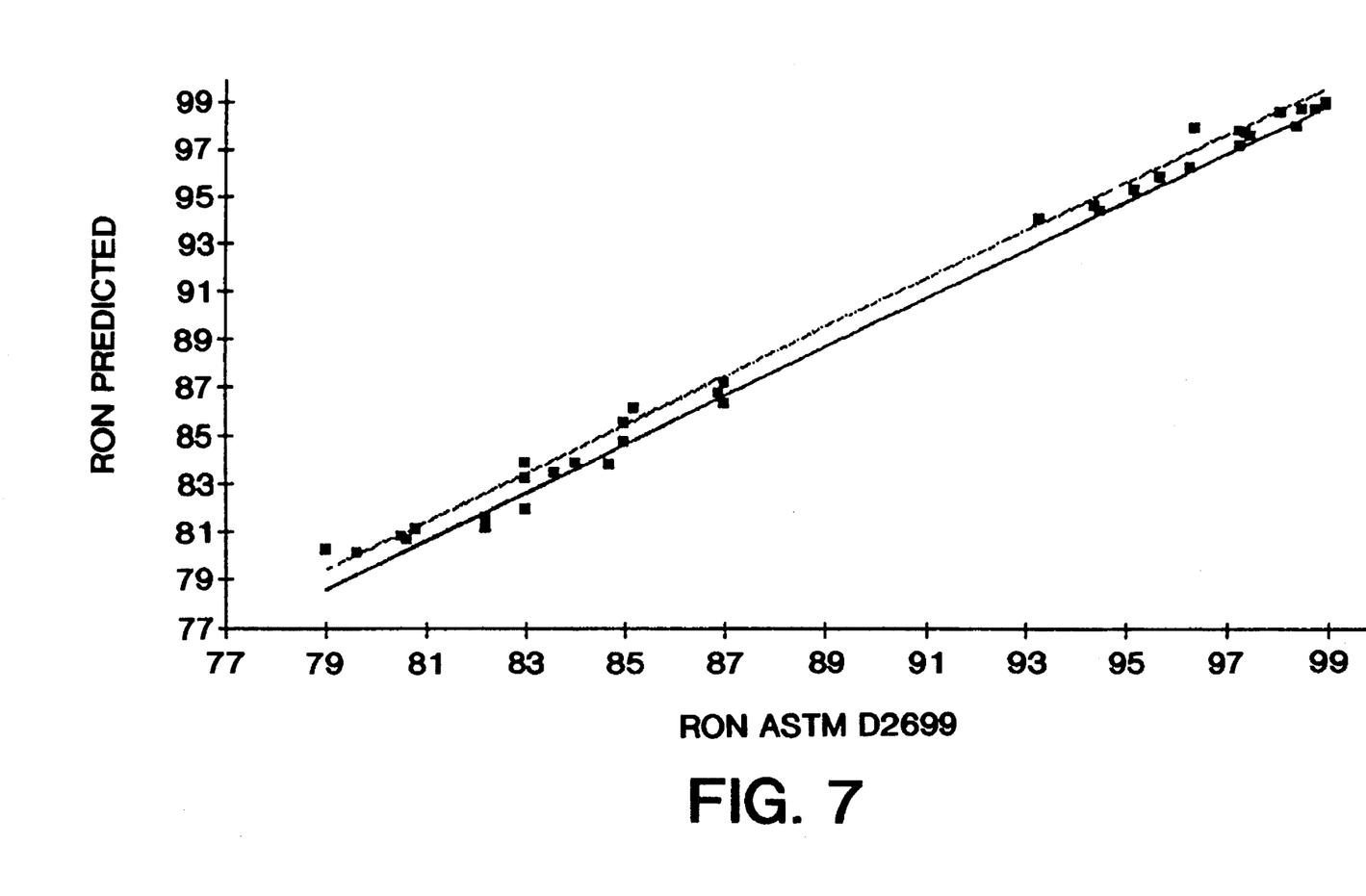
FIG. 7 illustrates RON values predicted according to the invention compared to actual RON values measured according to ASTM-2699.
Figure 9:
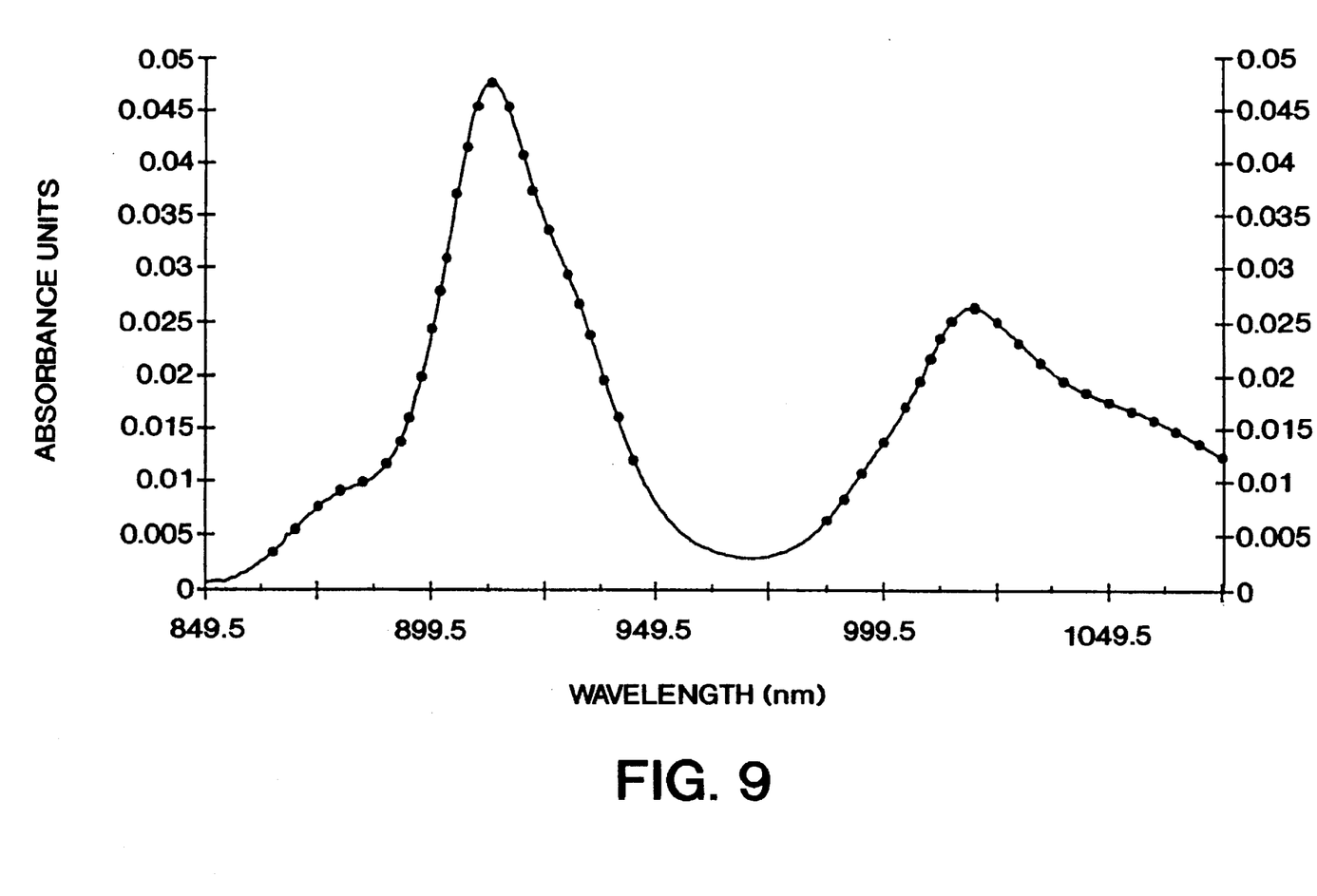
FIG. 9 illustrates the third overtone and its recombination bands for a typical process spectrum as illustrated in Example 2.

In this example research octane number (RON) is predicted according to the invention and compared to actual measurements taken according to ASTM D-2699. Predicted values are plotted versus determined values on FIG. 7. As shown, most values fall within the ASTM acceptance band. Further, as set forth above, the third overtone, in the spectral range of between about 800 nm to about 1050 nm, and its recombination bands is also suitable for providing predictions in accordance with the invention. In this example, RON is predicted from the third overtone, which is illustrated in FIG. 9.

Figure 8:
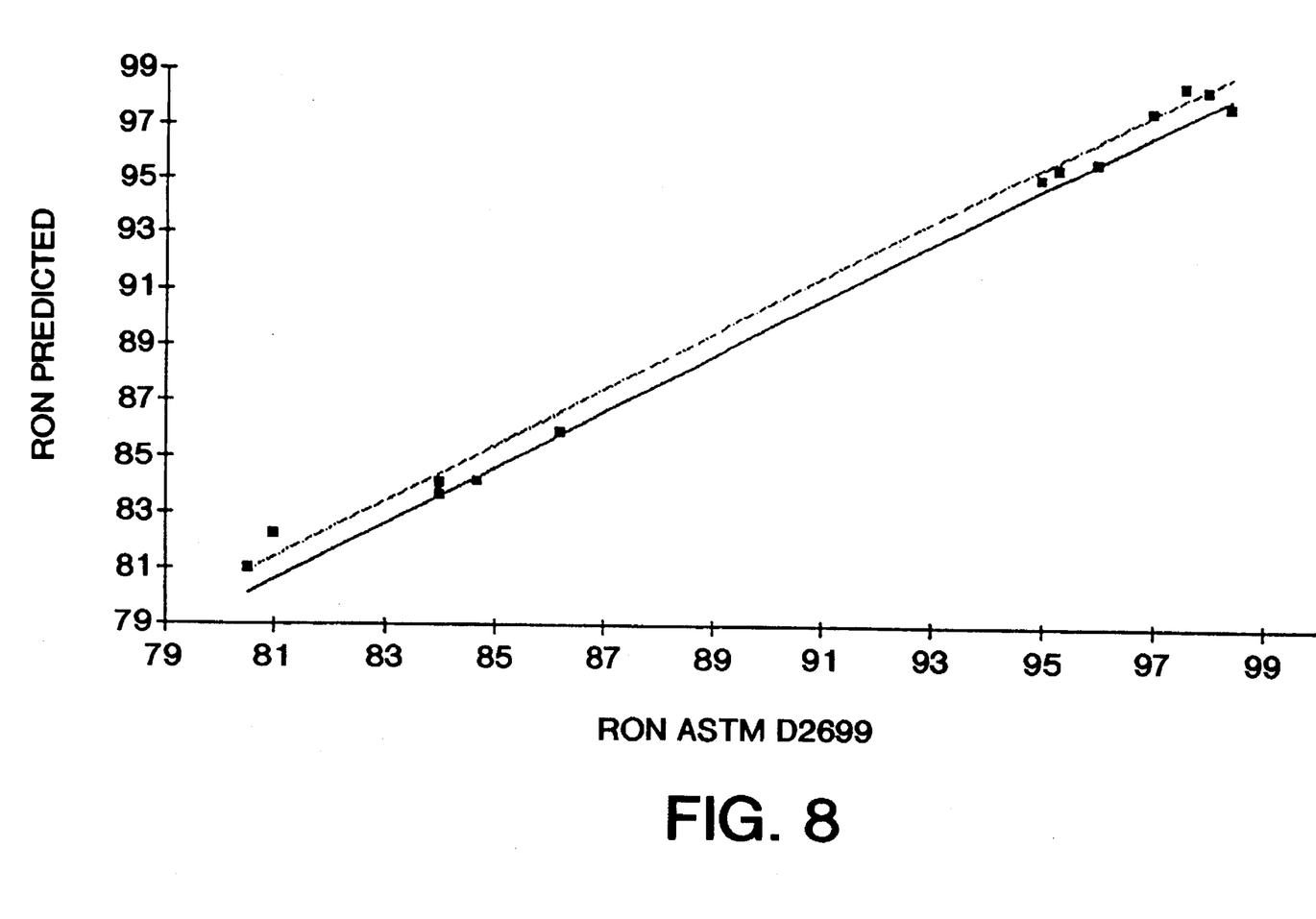
FIG. 8 illustrates predicted RON values of the validation set compared to actual ASTM determined RON.

In FIG. 8, values for the validation set are also plotted and also fall within the ASTM acceptance band.

The foregoing results were obtained while reducing the spectrum for each gasoline from 1600 points to 47 points for input to the network in a similar manner as was done while measuring RVP in Example 1 above.

Tables VI through IX set forth below contain prediction values and ASTM values for the training sets and validation sets for the neural network.

In Tables VI and VIII, predicted RON values are compared to corresponding ASTM values, which were used to build a neural network in accordance with the invention. The average error and standard deviation values were determined. These values were within the deviation tolerated by the ASTM test. RON values for independent subsets of gasolines were then predicted using the neural network. Table VII and IX set forth the predicted values and ASTM measured values. As can be seen, the results compare satisfactorily, thus indicating the favorable performance of the neural network according to the invention.

TABLE VI

| Gasoline Regular | RON ASTM D2699 | RON Predicted | Error |
|---|---|---|---|
| gM.001 | 79.6 | 79.6 | −0.002 |
| gM.002 | 79.0 | 79.0 | −0.009 |
| gM.003 | 80.5 | 80.4 | 0.060 |
| gM.004 | 82.2 | 82.2 | −0.009 |
| gM.006 | 83.0 | 83.0 | 0.019 |
| gM.008 | 81.0 | 81.0 | 0.014 |
| gM.009 | 80.6 | 80.7 | −0.075 |
| gM.010 | 80.8 | 80.7 | 0.059 |
| gM.011 | 83.6 | 83.6 | 0.026 |
| gM.012 | 84.7 | 84.4 | 0.298 |
| gM.014 | 84.0 | 83.8 | 0.209 |
| gM.015 | 85.0 | 84.8 | 0.184 |
| gM.018 | 83.0 | 82.8 | 0.160 |
| gM.020 | 84.0 | 84.1 | −0.082 |
| gM.021 | 85.2 | 85.8 | −0.605 |
| gM.022 | 86.2 | 85.9 | 0.273 |
| gM.023 | 86.9 | 86.8 | 0.098 |
| gM.025 | 87.0 | 86.9 | 0.094 |
| Average Error | 0.039 | | |
| Std Dev. Error | 0.2 | | |

TABLE VII

| Gasoline Regular | RON ASTM D2699 | RON Predicted | Error |
|---|---|---|---|
| gM.002 | 79.0 | 79.0 | −0.009 |
| gM.005 | 82.2 | 82.5 | −0.339 |
| gM.012 | 84.7 | 84.4 | 0.298 |
| gM.016 | 85.0 | 84.3 | 0.739 |
| gM.021 | 85.2 | 85.8 | −0.605 |
| Average Error | 0.017 | | |
| Std Dev. Error | 0.5 | | |

TABLE VIII

| Gasoline Super | RON ASTM D2699 | RON Predicted | Error |
|---|---|---|---|
| gA.001 | 95.0 | 95.2 | −0.195 |
| gA.002 | 94.4 | 94.3 | 0.059 |
| gA.003 | 93.3 | 93.6 | −0.284 |
| gA.004 | 94.5 | 94.4 | 0.106 |
| gA.005 | 95.3 | 95.1 | 0.214 |
| gA.006 | 95.2 | 95.2 | −0.021 |
| gA.007 | 95.7 | 95.5 | 0.220 |
| gA.008 | 96.0 | 96.1 | −0.122 |
| gA.010 | 96.3 | 96.2 | 0.053 |
| gA.011 | 96.4 | 96.7 | −0.289 |
| gA.012 | 97.3 | 97.3 | 0.024 |
| gA.014 | 95.7 | 97.6 | −0.116 |
| gA.015 | 97.0 | 97.4 | −0.386 |
| gA.016 | 97.4 | 97.6 | −0.239 |
| gA.017 | 98.4 | 98.1 | 0.261 |
| gA.019 | 98.5 | 98.5 | 0.036 |
| gA.020 | 97.6 | 97.8 | −0.247 |
| gA.022 | 98.8 | 98.5 | 0.257 |
| gA.023 | 99.0 | 99.0 | 0.050 |
| gA.025 | 98.0 | 97.8 | 0.167 |
| gA.026 | 98.1 | 98.3 | −0.215 |
| Average Error | −0.032 | | |
| Std Dev. Error | 0.2 | | |

TABLE IX

| Gasoline Super | RON ASTM D2699 | RON Predicted | Error |
|---|---|---|---|
| gA.013 | 97.3 | 97.9 | −0.573 |
| gA.018 | 98.4 | 97.8 | 0.647 |
| gA.021 | 98.5 | 98.6 | −0.118 |
| gA.024 | 99.0 | 98.9 | 0.060 |
| Average Error | 0.014 | | |
| Std Dev. Error | 0.5 | | |

Thus disclosed is a system and method for evaluating a substance such as a hydrocarbon fuel which provides accurate predictions of parameters even when such parameters are nonlinearly related to the NIR spectra used for the prediction.

It should also be noted that while this disclosure is made in terms of the preferred embodiment wherein hydrocarbon fuels are evaluated, the method according to the invention would of course be useful in evaluating other substances as well.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for evaluating a hydrocarbon fuel from a family of hydrocarbon fuels selected from the group consisting of gasoline, diesel fuel, kerosene, naphtha and jet fuel to determine a desired parameter selected from the group consisting of Reid vapor pressure, simulated distillation values, research octane number, motor octane number, oxygen content, specific gravity octane number, bromine number, aniline point, smoke point, and combinations thereof, comprising the steps of:

(1) providing a computer configured as a neural network;

(2) training the neural network so as to evaluate a hydrocarbon fuel from the family of hydrocarbon fuels to determine the desired parameter, said training comprising the steps of:

(a) selecting a plurality of hydrocarbon fuels from the family of hydrocarbon fuels to be evaluated;

(b) obtaining an NIR spectra for each of said plurality of hydrocarbon fuels;

(c) codifying each of the NIR spectra obtained by providing a base line correction and thereafter reducing the base line corrected spectra to a desired number of points corresponding to the parameters being evaluated;

(d) developing a first matrix from the desired number of points, said first matrix to be subsequently inputted to the neural network;

(e) obtaining a second matrix of parameter values from an analytical evaluation of the plurality of hydrocarbon fuels;

(f) processing the first matrix and the second matrix in the neural network to obtain a functional relationship between the first matrix and the second matrix so as to develop a weighted matrix; and (g) repeating steps (b) through (f) to obtain an optimal weighted matrix.

(3) comparing an NIR spectra from a hydrocarbon fuel selected from the family of hydrocarbon fuels with the optimal weight matrix in the neural network to obtain a predicted value of the desired parameters for the selected hydrocarbon fuel.

2. A method according to claim 1, wherein the codifying step includes reducing the signal to about 47 points.

3. A method according to claim 1, wherein the parameter to be determined is Reid vapor pressure and wherein the codifying step includes reducing the signal to between about 30 to about 100 points.

4. A method according to claim 1, wherein the parameter to be determined is research octane number and wherein the codifying step includes reducing the signal to between about 30 to about 100 points.

5. A method according to claim 1, further including selecting a parameter to be determined which is non-linearly related to the near-infrared signal.

6. A method according to claim 1, wherein the near-infrared signal is obtained at a wavelength of between about 800 nm to about 1600 nm.

7. A method according to claim 1, wherein the near-infrared signal is obtained at a wavelength of between about 800 nm to about 1050 nm.

8. A method according to claim 1, wherein the near-infrared signal is obtained at a wavelength of between about 1100 nm to about 1500 nm.

9. A method according to claim 1, wherein the near-infrared signal is obtained on line.

10. A method according to claim 1, wherein the step of obtaining the near-infrared signal comprises obtaining a transmissive near-infrared spectrum from the hydrocarbon.

11. A method according to claim 1, wherein the step of obtaining the near-infrared signal comprises obtaining a reflective near-infrared spectrum from the hydrocarbon.

12. A method according to claim 1, wherein the codifying step further includes the step of base line correcting the signal prior to reducing the signal to the number of points.

13. A method according to claim 1, wherein the step of providing the neural network comprises providing a neural network having an input layer, an intermediate layer, and an output layer, and wherein the input layer has between about 30 to about 100 nodes, the intermediate layer has between about 3 to about 15 nodes, and the output layer has a number of nodes equivalent to a number of desired parameters to be determined.

14. A method according to claim 1, wherein the step of providing the neural network includes providing a neural network having layers and having transfer functions between the layers which are sigmoid functions.

15. A method according to claim 14, wherein the sigmoid functions are as follows:

$$O_j = f\left( \sum_{i=0}^{n} W_{ji} \cdot I_i \right),$$

wherein i and j are nodes of the network;

$I_j$ is an output value of node i;

$W_{ji}$ is a weighted value between i and j; and $O_j$ is an output value of node j.

16. A method according to claim 15, wherein the sigmoid function includes a sigmoid transfer function as follows:

$$f(x) = \frac{1}{(1 - e^{(-x)})}.$$

wherein $$x = \left( \sum_{i=0}^{n} W_{ji} \cdot I_i \right).$$

* * * * *

UNITED STATES PATENT AND TRADEMARK OFFICE
CERTIFICATE OF CORRECTION

PATENT NO. : 5,572,030
DATED : November 5, 1996
INVENTOR(S) : Aaron Ranson et al.

It is certified that error appears in the above-identified patent and that said Letters Patent is hereby corrected as shown below:

In Claim 1, column 10, line 65, delete the "." and substitute therefor a --,--.

Signed and Sealed this

Fourteenth Day of September, 1999

Attest:

Q. TODD DICKINSON

*Attesting Officer*     Acting Commissioner of Patents and Trademarks